US009896450B2

(12) United States Patent
Rajashekara et al.

(10) Patent No.: US 9,896,450 B2
(45) Date of Patent: Feb. 20, 2018

(54) **MODULATORS OF *CLAVIBACTER MICHIGANENSIS* AND METHODS OF MAKING AND USING THEREOF**

(71) Applicant: Ohio State Innovation Foundation, Columbus, OH (US)

(72) Inventors: Gireesh Rajashekara, Wooster, OH (US); James R. Fuchs, Columbus, OH (US); Sally Miller, Wooster, OH (US); Corey Nislow, Vancouver (CA); Xiulan Xu, Beijing (CN)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/146,224

(22) Filed: May 4, 2016

(65) Prior Publication Data

US 2016/0326174 A1 Nov. 10, 2016

Related U.S. Application Data

(60) Provisional application No. 62/156,630, filed on May 4, 2015.

(51) Int. Cl.

| | | |
|---|---|---|
| *A01N 47/16* | (2006.01) | |
| *A01N 43/56* | (2006.01) | |
| *A01N 43/78* | (2006.01) | |
| *A01N 43/40* | (2006.01) | |
| *A01N 25/00* | (2006.01) | |
| *C07D 221/00* | (2006.01) | |
| *C07D 233/02* | (2006.01) | |
| *C07D 277/02* | (2006.01) | |
| *C07D 471/06* | (2006.01) | |
| *C07D 295/182* | (2006.01) | |
| *A01N 43/90* | (2006.01) | |
| *C07D 211/62* | (2006.01) | |
| *C07D 417/12* | (2006.01) | |
| *A01N 43/36* | (2006.01) | |
| *A01N 43/46* | (2006.01) | |
| *A01N 43/52* | (2006.01) | |

(52) U.S. Cl.
CPC ........... *C07D 471/06* (2013.01); *A01N 25/00* (2013.01); *A01N 43/36* (2013.01); *A01N 43/40* (2013.01); *A01N 43/46* (2013.01); *A01N 43/52* (2013.01); *A01N 43/56* (2013.01); *A01N 43/78* (2013.01); *A01N 43/90* (2013.01); *A01N 47/16* (2013.01); *C07D 211/62* (2013.01); *C07D 295/182* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 6,262,002 B1* | 7/2001 | Carey | .............. B09C 1/10 510/110 |
| 2011/0142883 A1* | 6/2011 | Dixit | .............. A61K 9/146 424/400 |

FOREIGN PATENT DOCUMENTS

WO WO 2014036443 A2 * 3/2014 ............. A61K 31/45

OTHER PUBLICATIONS

Aiello, et al., "Discovery and characterization of inhibitors of Pseudomonas aeruginosa type III secretion", Antimicrob Agents Chemother 54, 2010, 1988-1999.
Arnoldo, et al., "Identification of Small Molecule Inhibitors of Pseudomonas aeruginosa Exoenzyme S Using a Yeast Phenotypic Screen", PLoS Genet 4, 2008, e1000005.
Carlton, et al., "Ingress of *Clavibacter michiganensis* subsp. *michiganensis* into tomato leaves through hydathodes", Phytopathology 88, 1998, 525-529.
Chang, et al., "Dissemination of *Clavibacter michiganensis* subsp. *michiganensis* by practices used to produce tomato transplants", Phytopathology 81, 1991, 1276-1281.
Cooksey, "Genetic of bactericide resistance in plant pathogenic bacteria", Annu. Rev. Phytopathology 28, 1990, 201-219.
De La Fuente, et al., "Small molecules with antimicrobial activity against *E. coli* and *P. aeruginosa* identified by high-throughput screening", Br J Pharmacol. 55, 2006, 551-9.
Gartemann, et al., "*Clavibacter michiganensis* subsp. *michiganensis*: first steps in the understanding of virulence of a Gram-positive phytopathogenic bacterium", J Biol 106 (2-3), 2003, 179-191.
Gleason, et al., "Recent progress in understanding and controlling bacterial canker of tomato in Eastern North America", Plant Dis. 77, 1993, 1069-1076.
Hausbeck, et al., "Effect of bactericides on population sizes and spread of *Clavibacter michiganensis* subsp. *michiganensis* on tomatoes in the greenhouse and on disease development and crop yield in the field", Phytopathology 90, 2000, 39-44.
Hong-Geller, et al., "Small molecule to identify inhibitors of infectious disease", Drug Discovery. InTech, 2013, Chapter 5.
Junker, et al., "High-throughput screens for small-molecule inhibitors of Pseudomonas aeruginosa biofilm development", Antimicrob Agents Chemother 51(10), 2007, 3582-90.
Kamau, et al., "A Focused Small-Molecule Screen Identifies 14 Compounds with Distinct Effects on Toxoplasma gondii", Antimicrobial Agents and Chemotherapy 56(11), 2012, 5581-5590.
King, et al., "Antimicrobial properties of natural phenols and related compounds: obtusastyrene and dihydro-obtusastyrene", Antimicrob Agents Chemother. 1(3), 1972, 263-7.

(Continued)

*Primary Examiner* — Tracy Vivlemore
*Assistant Examiner* — Monica A Shin
(74) *Attorney, Agent, or Firm* — Meunier Carlin & Curfman LLC

(57) ABSTRACT

The subject matter disclosed herein generally relates to modulators of *Clavibacter michiganensis* subsp. *michiganensis*, derivatives thereof, formulations thereof, coated seeds, and methods of using such compounds to treat diseases such as bacterial canker in plants.

7 Claims, 6 Drawing Sheets

(56) References Cited

OTHER PUBLICATIONS

Lieberman, et al., "A small-molecule screen identifies the antipsychotic drug pimozide as an inhibitor of Listeria monocytogenes infection", Antimicrob Agents Chemother 53(2), 2009, 756-764.

Lipinski, et al., "Experimental and computational approaches to estimate solubility and permeability in drug discovery and development settings", Drug Deliv. Rev. 23, 1997, 3-25.

Louws, et al., "Rep-PCR-mediated genomic finger-printing: a rapid and effective method to identify *Clavibacter michiganensis* subsp. *michiganensis*", Phytopathology 88, 1998, 862-868.

Miller, et al., "Hot water and chlorine treatment of vegetable seeds to eradicate bacterial plant pathogens.", The Ohio State University Extension HYG-3085-05, 2005, p. 1-5.

Patel, et al., "Microwave-assisted synthesis of coumarin based 1,3,5-triazinyl piperazines and piperidines and their antimicrobial activities", Acta Poloniae Pharmaceutica—Drug Research 69, 2012, 879-891.

Pereira, et al., "High-throughput screening identifies novel inhibitors of the acetyl transferase activity of *Escherichia coli* GlmU", Antimicrob Agents Chemother 53, 2009, 2306-2311.

Phaechamud, et al., "Characterization and Antimicrobial Activity of N-Methyl-2-pyrrolidone-loaded Ethylene Oxide-Propylene Oxide Block Copolymer Thermosensitive Gel", Indian J Pharm Sci. 74(6), 2012, 498-504.

Sathiyanarayanan, et al., "Optimization and production of pyrrolidone antimicrobial agent from marine sponge-associated *Streptomyces* sp. MAPS15", Bioprocess Biosyst. Eng. 37(3), 2014, 561-73.

Schreiber, et al., "A high-throughput chemical screen for resistance to Pseudomonas syringae in *Arabidopsis*", Plant J. 54, 2008, 522-531.

Shimi, et al., "4,4'-isopropylidine-bis(2-isopropyl)phenol, a new inhibitor for cell wall formation of Bacillus subtilis", Antimicrob Agents Chemother 9(4), 1976, 580-584.

Wallace, et al., "Compound prioritization methods increase rates of chemical probe discovery in model organisms", Chemistry & Biology. 18(10), 2011, 1273-1283.

Xu, et al., "Bioluminescence imaging of *Clavibacter michiganensis* subsp. *michiganensis* infection of tomato seeds and plants", Appl Environ Microbiol 76(12), 2010, 3978-3988.

Zhang, et al., "A simple statistical parameter for use in evaluation and validation of high throughput screening assays", J. Biomol. Screen 4, 1999, 67-73.

Zikos, et al., "Commercially available chemicals as immunizing haptens for the development of a polyclonal antibody recognizing carbendazim and other benzimidazole-type fungicides", Chemosphere 119, 2015, p. 516-520.

Schreiber, et al., "Found in Translation: High-Throughput Chemical Screening in *Arabidopsis thaliana* Identifies Small Molecules That Reduce Fusarium Head Blight Disease in Wheat", Mol. Plant Microbe Interact. 24, 2011, 640-648.

* cited by examiner

MODULATORS OF *CLAVIBACTER MICHIGANENSIS* AND METHODS OF MAKING AND USING THEREOF

CROSS REFERENCE TO RELATED APPLICATIONS

This application claims the benefit of priority to U.S. Provisional Application 62/156,630, filed May 4, 2015, which is incorporated by reference herein in its entirety.

STATEMENT REGARDING FEDERALLY FUNDED RESEARCH

This invention was made with government support under grant number 2010-51181-21415 awarded by The United States Department of Agriculture National Institute of Food and Agriculture Specialty Crop Research Initiative. The government has certain rights in the invention.

FIELD

The subject matter disclosed herein generally relates to modulators of *Clavibacter michiganensis*, derivatives thereof, formulations thereof, coated and primed seeds, and methods of using such compounds to treat diseases such as bacterial canker in plants.

BACKGROUND

Tomato bacterial canker, caused by Gram-positive bacterium *Clavibacter michiganensis* subsp. *michiganensis* (Cmm), is one of the most important diseases of tomato in temperate zones and greenhouses worldwide (Gleason M L, et al., Recent progress in understanding and controlling bacterial canker of tomato in Eastern North America. Plant Dis. 1993, 77:1069-1076). Cmm infects the plant through wounds and via natural openings, such as stomata and hydathodes, after which it moves into xylem (Carlton W M, et al., Ingress of *Clavibacter michiganensis* subsp. *michiganensis* into tomato leaves through hydathodes. *Phytopathology* 1998, 88:525-529; Gartemann K H, et al., *Clavibacter michiganensis* subsp. *michiganensis*: first steps in the understanding of virulence of a Gram-positive phytopathogenic bacterium. *J. Biotechnol.* 2003, 106:179-191). Bacterial canker causes plant wilting and death, "bird's eye" lesions on the fruit (field) or netting (greenhouse), and reduced fruit set and size, which leads to severe yield loss, which can be as high as 84% in commercial fields and 93% in controlled studies. In the U.S., the economic loss due to bacterial canker reaches 25-30% in greenhouse tomato production.

The pathogen Cmm is seed-transmitted and infested seed and seedlings are considered the primary source of inoculum. It is known that Cmm is a strong endophyte and is easily disseminated directly into vascular tissue during transplanting, pruning, and harvesting under current tomato production systems (Chang R J, et al., Dissemination of *Clavibacter michiganensis* subsp. *michiganensis* by practices used to produce tomato transplants. Phytopathology. 1991, 81:1276-1281).

At present, control of tomato bacterial canker mainly relies on use of clean seed, healthy transplants and crop rotation. Once the disease is established in a field or greenhouse, however, chemical treatment such as copper-based bactericides or antibiotics has limited effect in reducing the disease (Hausbeck M J, et al., Effect of bactericides on population sizes and spread of *Clavibacter michiganensis* subsp. *michiganensis* on tomatoes in the greenhouse and on disease development and crop yield in the field. *Phytopathology.* 2000, 90:39-44; Miller, S. A., et al., Hot water and chlorine treatment of vegetable seeds to eradicate bacterial plant pathogens. The Ohio State University Extension. HYG-3085-05, 2005). Meanwhile, the development of bactericide resistance in plant pathogenic bacteria is increasing (Cooskey D A, Genetic of bactericide resistance in plant pathogenic bacteria. Annu. Rev. *Phytopathology.* 1990, 28:201-219).

Other subspecies of *Clavibacter michiganensis* are problematic for a variety of other economically important plants. For example, *Clavibacter michiganensis* subsp. *nebraskensis*, which affects maize, *Clavibacter michiganensis* subsp. *phaseoli* subsp. *nov.*, which affects beans, *Clavibacter michiganensis* subsp. *sepedonicus*, which affects potatoes, *Clavibacter michiganensis* subsp. *tesselarius*, which affects wheat, and *Clavibacter michiganensis* subsp. *insidiosus*, which affects alfalfa, all present challenges that need addressing.

Therefore, new chemicals with unique targets or target pathways are urgently required for management of *Clavibacter michiganensis* infections. The compositions and methods disclosed herein address these and other needs.

SUMMARY

In accordance with the purposes of the disclosed materials, compounds, compositions, kits, and methods, as embodied and broadly described herein, the disclosed subject matter relates to compositions, methods of making said compositions, and methods of using said compositions. More specifically, modulators of *Clavibacter michiganensis*, are provided herein, as well as various derivatives of these modulators. Formulations comprising the disclosed modulators are also disclosed. Also disclosed are seeds treated with or coated with the disclosed modulators. Methods of treating, priming, or coating seeds with the disclosed modulators are also described herein. Further, disclosed herein are methods of using modulators of *Clavibacter michiganensis* to treat diseases such as bacterial canker in plants.

Additional advantages will be set forth in part in the description that follows or may be learned by practice of the aspects described below. The advantages described below will be realized and attained by the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

Figure 1:
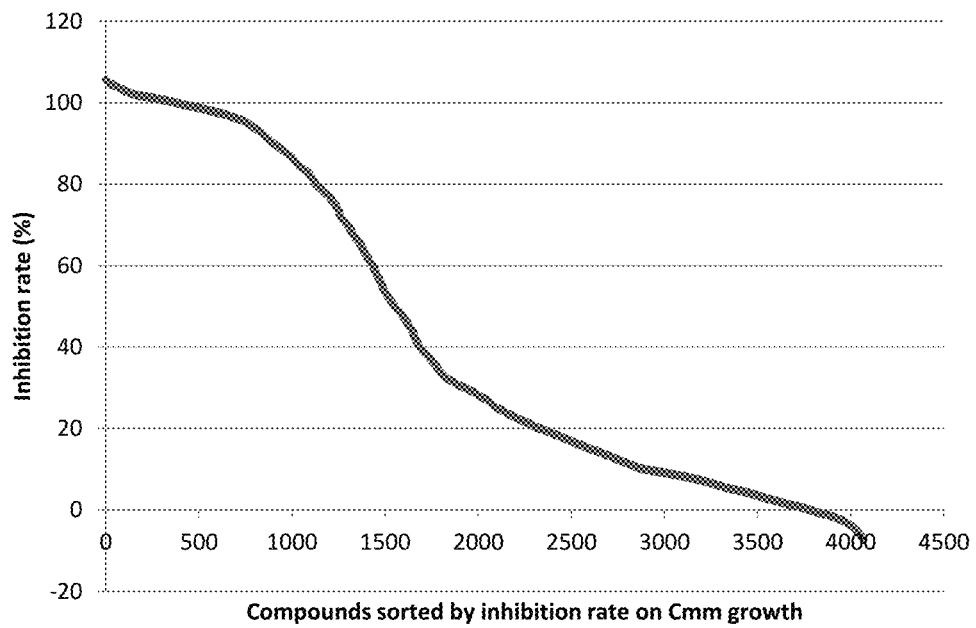
FIG. 1 is a graph showing the inhibition rate in an initial screen of 4,182 compounds on Cmm (strain C290) growth. Small molecules with inhibition rate over 99% were considered as candidates for further analysis.

The materials, compounds, compositions, articles, and methods described herein may be understood more readily by reference to the following detailed description of specific aspects of the disclosed subject matter and the Examples included therein.

Before the present materials, compounds, compositions, kits, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

By "reduce" or other forms of the word, such as "reducing" or "reduction," is meant lowering of an event or characteristic (e.g., bacterial canker). It is understood that this is typically in relation to some standard or expected value, in other words it is relative, but that it is not always necessary for the standard or relative value to be referred to. For example, "reduces Cmm" means reducing the rate of growth of Cmm relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., Cmm growth or survival). The term "control" is used synonymously with the term "treat."

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as ($Z^1Z^2$)C=C($Z^3Z^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C═O.

The terms "amine" or "amino" as used herein are represented by the formula $—NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" or "carboxyl" group as used herein is represented by the formula $—C(O)O^-$.

The term "ester" as used herein is represented by the formula $—OC(O)Z^1$ or $—C(O)OZ^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula $—NO_2$.

The term "silyl" as used herein is represented by the formula $—SiZ^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula $—S(O)_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula $—S(O)_2NH—$.

The term "phosphonyl" is used herein to refer to the phospho-oxo group represented by the formula $—P(O)(OZ^1)_2$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "thiol" as used herein is represented by the formula —SH.

The term "thio" as used herein is represented by the formula —S—.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxyl group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

A library containing 4,182 compounds that have been identified as bioactive in *Saccharomyces cerevisiae* was tested in a high-throughput primary screen against a *Clavibacter michiganensis* subsp. *michiganensis* (Cmm) wild-type strain C290 by whole-cell growth inhibition. There were 468 molecules (11.2% hit rate) identified in the primary screen that possessed -cidal or -static effects on Cmm growth at a final concentration of 100 μM and 77 candidate molecules were selected based on Golden Triangle analyses for secondary screening.

Secondary screens showed that selected candidates effectively killed multiple Cmm strains as well as *Bacillus subtilis*, but most compounds did not affect growth of *Pseudomonas fluorescens, Mitsuaria* sp., *Lysobacterenzymogenes, Lactobacillus rhamnosus, Bifidobacteria animalis*, or *Escherichia coli*. In addition, the majority of the candidate compounds showed no phytotoxcity on either tomato or *Arabidopsis*.

A 96-well seedling assay using a bioluminescent Cmm strain and in vivo imaging system was used to rapidly evaluate compound effects on Cmm infection in tomato seedlings. The 12 most potent novel molecules were prioritized based on the total score evaluated in the secondary screen and reduction of the pathogen infection in planta. Based on their potency and specificity, these compounds also represent chemical scaffolds for derivatives of Cmm-specific bactericides.

In specific examples, disclosed herein are modulators having Formula I:

I 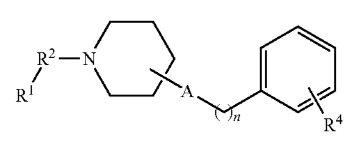 wherein

A is $—C(O)—NR^3—$ or $—NR^3—C(O)—$;

n is 0, 1, or 2;

R¹ is an aryl or heteroaryl, optionally substituted with one or more hydroxyl, halogen, alkyl, alkenyl, alkynyl, alkoxyl, alkenyloxyl, amino, aminoalkyl, aminoalkenyl, cycloalkyl, cycloalkenyl, alkylcarboxylate, cycloalkylcarboxylate, alkylcarbonate, cycloalkylcarbonate, amidoalkyl, amidocycloalkyl, aryl or heteroaryl;

R² is a $C_{1-4}$ alkylene, $C_{1-4}$ alkoxylene, or C3-5 alkenylene, optionally substituted with hydroxyl, halogen, oxo, amino, or $C_{1-6}$ alkyl;

R³ is H or $C_{1-6}$ alkyl; and

R⁴ is an aryl or heteroaryl, optionally substituted with one or more hydroxyl, halogen, alkyl, alkenyl, alkynyl, alkoxyl, alkenyloxyl, amino, aminoalkyl, aminoalkenyl, cycloalkyl, cycloalkenyl, alkylcarboxylate, cycloalkylcarboxylate, alkylcarbonate, cycloalkylcarbonate, amidoalkyl, amidocycloalkyl, aryl or heteroaryl;

or an agriculturally suitable salt thereof.

In specific examples of Formula I, A is —C(O)—NR³—. In other examples of Formula I, A is —NR³—C(O)—. A can be present at the 2, 3, or 4 position of the piperidine ring.

In specific examples of Formula I, n is 0.

In specific examples, R¹ can be substituted phenyl. In other examples, R¹ can be a substituted heteroaryl, such as pyrimidyl. In further examples, R¹ can be phenyl substituted with from 1 to 5 substituents, preferably from 1 to 3 substituents, more preferably 1 or 2 substituents. The substituents can be independently chosen from hydroxyl, halogen, alkyl, alkenyl, alkynyl, alkoxyl, alkenyloxyl, amino, aminoalkyl, aminoalkenyl, cycloalkyl, cycloalkenyl, alkylcarboxylate, cycloalkylcarboxylate, alkylcarbonate, cycloalkylcarbonate, amidoalkyl, amidocycloalkyl, aryl or heteroaryl. For example, R¹ can be is a phenyl or heteroaryl substituted with one or more substituents chosen from F, Cl, Br, OH, $C_{1-8}$ alkyl, $C_{1-8}$ alkenyl, $C_{1-8}$ alkynyl, $OC_1$-$C_8$ alkyl, $OC_{2-8}$ alkenyl, $NH_2$, $NHC_1$-$C_8$ alkyl, $NHC_2$-$C_8$ alkenyl, $C_{5-6}$ cycloalkyl, $C_{5-6}$ cycloalkenyl, $COC_{1-8}$ alkyl, $COC_{5-6}$ cycloalkyl, $CO_2C_{1-8}$ alkyl, $CO_2C_{5-6}$ cycloalkyl, $CONHC_{1-8}$ alkyl, $CONHC_{5-6}$ cycloalkyl, or CONHphenyl. In a specific example, R¹ can be a fluoro and methoxyl substituted phenyl, a hydroxyl substituted phenyl, or a fluorosubstituted phenyl.

In specific examples, R² can be methylene, ethylene, propylene, butylene, propenylene, buteneylene, or pentenylene, optionally substituted with hydroxyl, F, Cl, Br, oxo (=O), amino, or $C_{1-6}$ alkyl. In other examples R² is optionally substituted propylenyl or propyloxyl. In a preferred example, R² is methylene (—CH₂—).

In specific examples, R⁴ can be substituted phenyl. In other examples, R⁴ can be a substituted or unsubstituted heteroaryl, such as pyrimidyl or thiazolyl. In further examples, R⁴ can be phenyl substituted with from 1 to 5 substituents, preferably from 1 to 3 substituents, more preferably 1 or 2 substituents. The substituents can be independently chosen from hydroxyl, halogen, alkyl, alkenyl, alkynyl, alkoxyl, alkenyloxyl, amino, aminoalkyl, aminoalkenyl, cycloalkyl, cycloalkenyl, alkylcarboxylate, cycloalkylcarboxylate, alkylcarbonate, cycloalkylcarbonate, amidoalkyl, amidocycloalkyl, aryl or heteroaryl. For example, R⁴ can be a phenyl or heteroaryl substituted with one or more substituents chosen from F, Cl, Br, OH, $C_{1-8}$ alkyl, $C_{1-8}$ alkenyl, $C_{1-8}$ alkynyl, $OC_1$-$C_8$ alkyl, $OC_{2-8}$ alkenyl, $NH_2$, $NHC_1$-$C_8$ alkyl, $NHC_2$-$C_8$ alkenyl, $C_{5-6}$ cycloalkyl, $C_{5-6}$ cycloalkenyl, $COC_{1-8}$ alkyl, $COC_{5-6}$ cycloalkyl, $CO_2C_{1-8}$ alkyl, $CO_2C_{5-6}$ cycloalkyl, $CONHC_{1-8}$ alkyl, $CONHC_{5-6}$ cycloalkyl, or CONHphenyl. In a specific example, R⁴ can be a methoxyl substituted phenyl or a thiazolyl.

Specific examples of compounds of Formula I include:

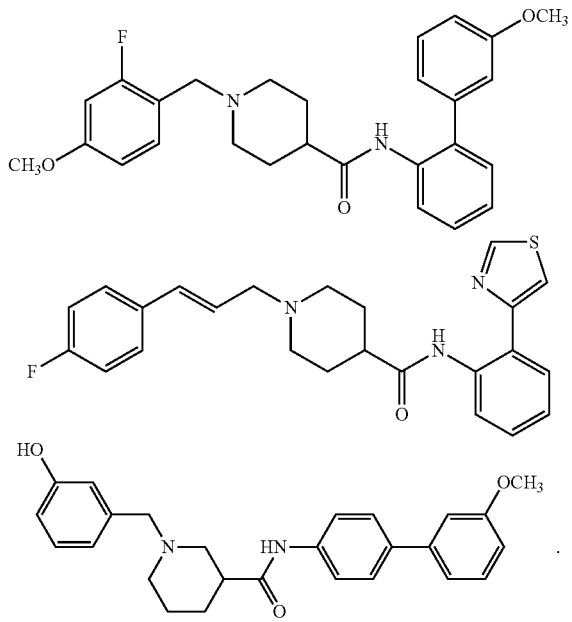

Further, disclosed herein are modulators having Formula II:

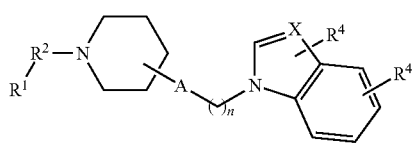

wherein A, n, R¹, R², and R⁴ are as defined above in Formula I, and X is N or CH. A specific example of a compound of Formula II is

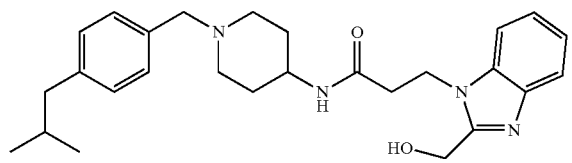 [SMILES: CC(C)Cc1ccc(CN2CCC(NC(=O)CCn3c(CO)nc4ccccc43)CC2)cc1]

Further, disclosed herein are modulators having Formula III:

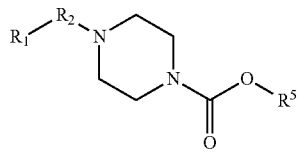

wherein R¹ and R², are as defined above in Formula I, and R⁵ is a $C_{1-8}$ alkyl, a $C_{3-6}$ cycloalkyl, or phenyl, optionally substituted with halogen, hydroxyl, $C_{1-8}$ alkyl, $C_{1-8}$ alkoxyl, or amine. A specific example of a compound of Formula III is

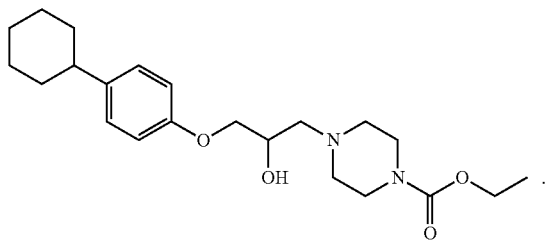 [SMILES: CCOC(=O)N1CCN(CC(O)COc2ccc(C3CCCCC3)cc2)CC1]

Further, disclosed herein are modulators having Formula IV:

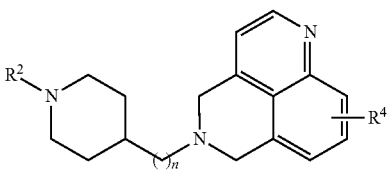
IV wherein $R^2$, $R^4$, and n are as defined above in Formula I. A specific example of a compound of Formula IV is

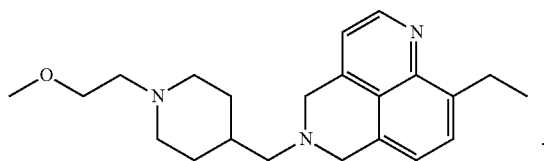 [SMILES: CCc1ccc2c3c(ccnc13)CN(CC1CCN(CCOC)CC1)C2]

Also disclosed herein are modulations having the following structures:

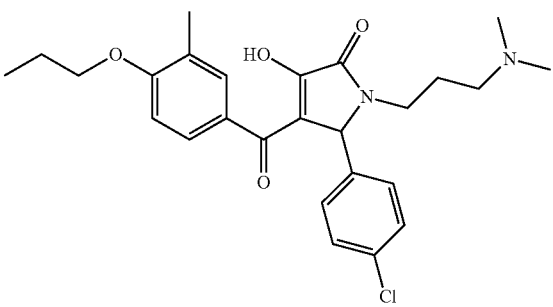

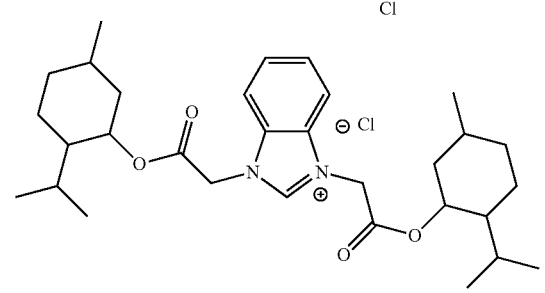

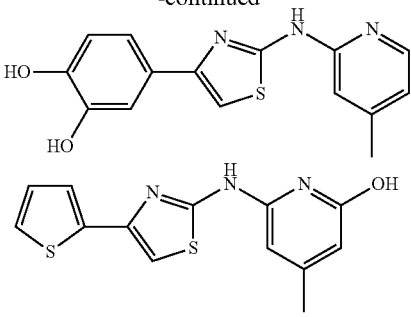

Formulations

The disclosed modulators can be formulated into a form for delivery into the soil or for coating onto seeds. For example, disclosed are formulations comprising a modulator as disclosed herein and a soil-compatible carrier. The solid soil-compatible carrier can be, but is not limited to, bran, starch, cellulose, alginate, clay, pectin, carboxy methyl cellulose and mixtures thereof. The formulations can also comprise seeds. Also, seeds (e.g., tomato) can be coated with the modulators disclosed herein. Coating of seeds can be performed by methods disclosed in the art, such as by soaking the seeds or spraying the seeds with a composition comprising the disclosed modulators. Polymers, clays and waxes can be used to help the compositions adhere to the seeds. The coated seeds can also be part of a solid matrix that is applied to soil. The coating can further comprise additives such as carbohydrate compounds useful for enhancing survival after temporary rehydration or contact with growth medium. Carbohydrates include gums, sugars, starches, and celluloses, particularly gum arabic, xanthan gum, sucrose, mannitol, maltose, trehalose, dextrin, dextran, and carboxymethylcellulose. The seeds can be dried after the composition has been applied. The coated seeds can be rehydrated for planting or exposed to hydration after planting.

The disclosed compounds can also be used to prime seeds. That is, the disclosed compounds can be used alone or with plant nutrients, and delivered to the seed embryo by imbibing. Seed priming with the disclosed compounds can be done by any of the four common methods utilized for priming seeds: hydropriming, osmotic priming, solid matrix priming, or drum priming. Hydropriming is the simple soaking of seeds in water with the disclosed compounds.

This process is especially useful in economically disadvantaged, arid crop growing areas. Osmotic priming, also called osmopriming or osmoconditioning, is the soaking of seeds in solutions with the disclosed compounds and also containing chemicals such as mannitol, potassium nitrate ($KNO_3$), potassium chloride (KCl), polyethylene glycol (PEG), or sodium chloride (NaCl). Plant hormones, which control or affect various stages of seed germination, or beneficial microorganisms (which help control fungal and bacterial disease) can be added to the osmopriming solutions. Solid matrix priming involves the incubation of seeds in a solid, insoluble matrix, such as vermiculite, diatomaceous earth, or another highly water absorbent polymer, with a limited amount of water, allowing for slow imbibition of the disclosed compounds. In drum priming, seeds are hydrated by placing them in a rotating drum with the disclosed compounds into which a controlled level of water vapor is released.

Additional Agents

The compositions disclosed herein comprise a modulator as disclosed herein and one or more surface active agents. The surface active agents disclosed herein can assist in uniformly delivering the disclosed modulators to the plant cells, either intracellular agents or extracellular agents. The term "surface active agent" includes any surface active ingredient, inter alia, wetting agents, surfactants, and the like. Active agents that are characterized as "wetting agents" can also be characterized by others as "surfactants." The agents of the present disclosure are capable of providing a continuous solution that does not develop phases when the compositions are applied to the plant.

No two plants have identical surface compositions. Even within a subgenus of plants, the variability in plant surface can be dramatic. In addition, some plant cells are covered with a hydrophobic waxy resin, while others are more porous. The compositions disclosed herein are capable of delivering by way of a surface active agent, the combination of active agents further described herein.

The compositions disclosed herein comprise one or more carriers. One embodiment comprises water as the carrier. In another embodiment the carrier comprises water and a co-solvent. The co-solvent can be an alcohol, inter alia, methanol, ethanol, or the like.

Methods of Use

The disclosed compounds can be used to treat *Clavibacter michiganensis* infections in various plants. For example, the disclosed compounds can be used to treat *Clavibacter michiganensis* subsp. *nebraskensis*, which affects maize, *Clavibacter michiganensis* subsp. *phaseoli* subsp. *nov.*, which affects beans, *Clavibacter michiganensis* subsp. *sepedonicus*, which affects potatoes, *Clavibacter michiganensis* subsp. *tesselarius*, which affects wheat, and *Clavibacter michiganensis* subsp. *insidiosus*, which affects alfalfa. For example, the disclosed compounds can be used to treat tomato bacterial canker caused by *Clavibacter michiganensis* subsp. *michiganensis*. The disclosed compounds can be applied as a seed treatment by seed soaking and seed coating, or as foliar applications in seedlings. The amount of modulator disclosed herein that can be used can vary depending on the type of seeds, the amount or risk of infection, the climate, the soil, and other factors. The skilled artisan can determine the amount of modulators to use based on these factors. As an example, concentrations of modulator ranging from 1 µM to 1000 µM can be used.

Kits

Also provided herein are kits for treating or preventing *Clavibacter michiganensis* infection in plants. A kit can include any of the compounds or compositions described herein. A kit can further include one or more anti-bacterial agents, surfactants, anti-transpirants, nutrients, and the like. A kit can also include seeds of a plant, which can be treated or coated with the compounds or compositions disclosed herein. A kit can additionally include directions for use of the kit.

The examples below are intended to further illustrate certain aspects of the methods and compounds described herein, and are not intended to limit the scope of the claims.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

To facilitate data analysis, nominal scales on growth inhibition in the secondary screen were transformed to ordinal scores. The compound effect on Cmm growth was scored as "cidal"=4, "static"=3, "inhibition"=2 and "no effect"=1, and the effect on plant beneficial bacteria and human gut bacteria growth as scored as "cidal"=1, "static"=2, "inhibition"=3 and "no effect"=4. The compound effect on seed germination of tomato and *Arabidopsis* was scored as "germination rate (GR)=100%"=4, "100%>GR≥80%"=3, "80%>GR≥50%"=2, "GR<50%"=1. The total score of each compound was added up from the specificity, sensitivity and phytotoxicity tests carried in the secondary screen. The cytotoxicity of the most potent compounds was analyzed by one-way analysis of variance with mean separation by a least significant difference test at 5% level of significance in Minitab 16 statistical analysis software.

Example 1

Primary Screen

Small, drug-like molecules (e.g. less than 500 Da with a c Log P less than 5) are particularly attractive because they can often pass through cell membranes. Successful examples include inhibitors to Type III Secretion and biofilm formation by *Pseudomonas aeruginosa* (Aiello D, et al., Discovery and characterization of inhibitors of *Pseudomonas aeruginosa* type III secretion. *Antimicrob Agents Chemother.* 2010, 54:1988-1999; Arnoldo A, et al., Identification of small molecule inhibitors of *Pseudomonas aeruginosa* exoenzyme S using a yeast phenotypic screen. 2008, *PLoS Genet* 4 e1000005; Junker L M, et al., High-throughput screens for small-molecule inhibitors of Pseudomonas aeruginosa biofilm development. *Antimicrob Agents Chemother.* 2007, 51(10):3582-90), and novel kinase inhibitors to *Toxoplasma gondii* and acetyl transferase inhibitors in *E. coli* (Kamau E T, et al., A focused small-molecule screen identifies 14 compounds with distinct effects on *Toxoplasma gondii*. *Antimicrob Agents Chemother.* 2012, 56(11):5581-5590; Pereira M P, et al., High-throughput screening identifies novel inhibitors of the acetyl transferase activity of *Escherichia coli* GlmU. *Antimicrob Agents Chemother.* 2009, 53:2306-2311). Identification of "hits" from such HTP screens can provide the starting point for chemical tools to probe mechanisms of action and for drug development for infectious diseases.

A limited number of studies have used HTP screening in plant-pathogen models. Schreiber et al., (A high-throughput chemical screen for resistance to *Pseudomonas syringae* in *Arabidopsis*. Plant J. 2008, 54: 522-531) developed a 96-well plate liquid assay to screen small molecules that prevent symptoms caused by *Pseudomonas syringae* on *Arabidopsis thaliana* and uncovered a family of sulfanilamide compounds that reduce bacterial virulence in planta. Using a similar approach, further investigation of small molecules targeting the fungal phytopathogen *Fusarium graminearum* identified two compounds, sulfamethoxazole and indole alkaloid gramine, which reduced pathogen infection in wheat (Schreiber K J., et al., Found in translation: high-throughput chemical screening in *Arabidopsis thaliana* identifies small molecules that reduce *Fusarium* head blight disease in wheat. Mol. Plant Microbe Interact. 2011, 24:640-648). Nonetheless, no studies have been reported that identify small molecules that interact with plant pathogenic Gram-positive bacteria.

In this study, a validated library of 4,182 yeast-active molecules or, "yactives" (Wallace IM, et al., Compound prioritization methods increase rates of chemical probe discovery in model organisms. Chemistry & biology. 2011, 18(10): 1273-1283) was screened against Cmm by using a whole-cell based HTP screening approach and 77 of the 468 hits were further evaluated for their sensitivity, specificity, and phytotoxicity. Candidates were further tested for cytotoxicity and for Cmm inhibition in tomato seedlings using a bioluminescent Cmm strain. A structural analysis of the 12 most promising small molecules identified chemical scaffolds for potential bactericide development for future applications.

Specifically, a small molecule library containing 4,182 compounds was designed in collaboration with ChemBridge (San Diego, Calif.) and was supplied in a 96-well format in 10 mM in dimethyl sulfoxide (DMSO). Bacterial strains used in this study are listed in Table 1. Bacterial strains were streaked out from −80° C. freezer stock onto nutrient broth-yeast agar (NBY) and LB.

TABLE 1

List of bacterial strains tested in the primary and secondary screens.

| Bacteria | Strain | Reference |
|---|---|---|
| *Clavibacter michiganensis* subsp. *michiganensis* | C290 | Louws F, et al., Rep-PCR-mediated genomic finger-printing: a rapid and effective method to identify *Clavibacter michiganensis* subsp. *michiganensis*. Phytopathology 1998, 88: 862-868 |
| | BL-Cmm17 | Xu X, et al., Bioluminescence imaging of *Clavibacter michiganensis* subsp. *michiganensis* infection of tomato seeds and plants. Appl Environ Microbiol. 2010, 76(12): 3978-88 |
| | A226, A300 CMM12B | Louws, 1998 |
| | 08-687, 09-158, 09-159, VF3-1-08, VF6-7-08, 09-176, SM101-09, 09-157 SM287-11, SM288-11, SM610-11, SM611-11, SM614-11, SM615-11 | Different clonal groups of Cmm strains isolated from greenhouse tomatoes in US, Canada and Guatemala |
| *Pseudomonas fluorescens* | Wood1 | Plant beneficial bacteria, provided by Dr. Brain Mcspadden Gardener |
| *Bacillus subtilis* | GB03 | |
| *Mitsuaria* sp. | H24L5A | |
| *Lysobacter enzymogenes* | C3 | |
| *Lactobacillus rhamnosus* | LGG | Human gut bacteria, lab collection |
| *Bifidobacteranimalis* | Bb12 | |
| *Escherichia coli* | Nissle | |

Primary screening was conducted with Cmm wild-type strain C290, which was originally isolated from tomato in Ohio and characterized as type C by REP-PCR (Louws, et al., 1998). Briefly, a fresh bacterial culture was inoculated into 5 ml NBY broth and grown at 28° C. with shaking at 200 rpm. After 24 hours of incubation, the culture was diluted in NBY broth to an $OD_{600}$ of 0.05. To an aliquot of 100 μL diluted culture in each well in a 96-well plate, 1 μL of compound was added using a slotted pin tool (V and P Scientific, San Diego, Calif.) for a final concentration of 100 μM. Controls (four replicates/plate) containing 1 μL DMSO, 1 μL chloramphenicol (20 μg/μL), no compound and 100 μL of cell-free media were included in each test plate. Plates were incubated at 28° C. with shaking at 200 rpm for 24 hours. The end-point $OD_{595}$ was measured using a SUN-RISE™ Tecan kinetic microplate reader (Tecan US Inc., CA). A parameter Z' to evaluate the quality of the HTP screen was calculated using formula 1 (Zhang J H, et al., A simple statistical parameter for use in evaluation and validation of high throughput screening assays. *J. Biomol. Screen.* 1999, 4:67-73). The growth inhibition rate was calculated as described by formula 2. The culture in wells with ≥99% growth inhibition was streaked onto fresh NBY agar, as were the sterility, antibiotic and no compound control wells. Bacterial growth was measured on the plate after 48 hours at 28° C. Based on the recovery of Cmm on NBY, the compound was scored as either "static" or "cidal"

$$Z' = \frac{1 - (3\sigma_{c+} + 3\sigma_{c-})}{|\mu_{c+} - \mu_{c-}|} \quad \text{Formula (1)}$$

where $\sigma_{c+}$, $\sigma_{c-}$, $\mu_{c+}$, and $\mu_{c-}$ are the standard deviation and average of positive (DMSO amended) and negative controls (chloramphenicol amended).

$$\text{Inhibition rate} = \frac{(\mu_{c+} - X)}{(\mu_{c+} - \mu_{c-})} \times 100\% \quad \text{Formula (2)}$$

where $\mu_{c+}$, and $\mu_{c-}$ are the average OD of positive and negative controls, X is the OD in well with the small molecule compound.

Figure 8:
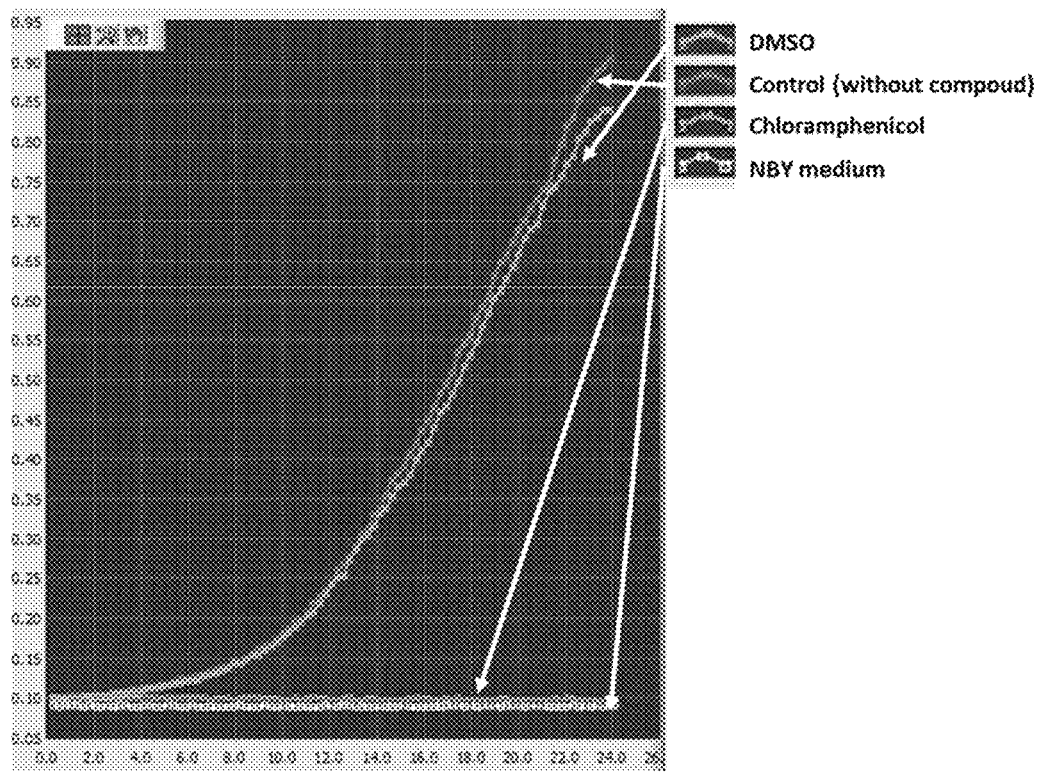
FIG. 8 displays that the growth of Cmm strain C290 in 96 well plates was not significantly affected by DMSO. Data acquired every 15 mins over 24 hour.
Figure 9:
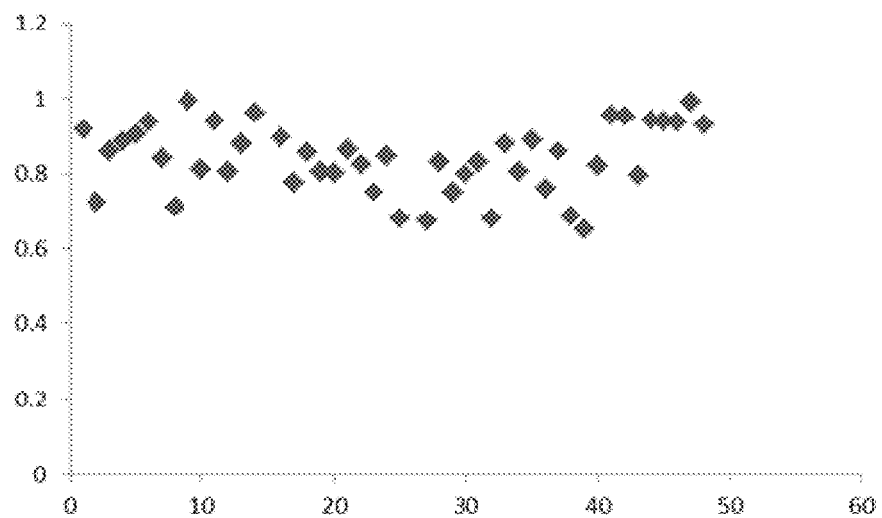
FIG. 9 displays the statistical parameter Z'-factor for individual library compound plates screened. The cell-based growth primary screen in this study had an average Z'=0.82. A Z' value >0.5 was considered acceptable.

As all small molecules were dissolved in DMSO, it was important to confirm whether Cmm growth was affected by DMSO. The supplement of 1 µL DMSO in 100 µL culture did not significantly affect Cmm growth in vitro (FIG. 8). The initial screen was an evaluation of growth by measuring the end-point $OD_{595}$ value and the average of the statistical parameter Z'-factor was 0.82 (FIG. 9). Z'-factor described the signal window and variation within the positive and negative controls and a Z' value higher than 0.5 was considered a robust HTP assay (Zhang J H, et al., A simple statistical parameter for use in evaluation and validation of high throughput screening assays. *J. Biomol. Screen.* 1999, 4:67-73). Compounds exhibiting high inhibition of growth (>99% inhibition) were considered candidates for future evaluations. With this criterion, 468 hits were identified in the primary screen (FIG. 1). Among these candidates, 350 exhibited a "static" effect, for which Cmm was revived after streaking onto a new NBY plate; and 118 were "cidal" to Cmm growth, in that Cmm was not revived after streaking.

Example 2

Secondary Screen with Selected Compounds

A structural analysis of the primary screen data for 468 hit compounds was conducted. The structural descriptor strings (SMILES) were subsequently converted into ChemDraw structures using ChemDraw for Excel. The compounds were exported to ChemDraw as a SD file using ChemFinder. ChemFinder resulted in the rapid identification of compounds containing the same structural motifs. The ChemDraw files of the hits were manually sorted into structural groups to establish preliminary structure-activity relationships (SAR). Finally, hits were prioritized for secondary screens based on their adherence to Lipinski's rule of 5. (Lipinski C A, et al., 1997. Experimental and computational approaches to estimate solubility and permeability in drug discovery and development settings. *Adv. Drug Deliv. Rev.* 1997, 23:3-25).

Seventy-seven selected compounds were re-ordered from ChemBridge in a 96-well format as a powder. The compounds were dissolved in 100 µL DMSO and stored at −80° C. until used. Four tests were carried out to evaluate the sensitivity and specificity of selected compounds, including 1) testing against multiple Cmm strains from different clonal groups as listed in Table 1; 2) testing the minimum inhibitory concentration for Cmm growth; 3) testing effects on growth of plant beneficial bacteria and human gut bacteria listed in Table 1, and 4) testing the cytotoxicity of the most potent compounds to Caco-2 cells.

Screening for growth inhibition of Cmm strains, plant beneficial bacteria and human gut bacteria was set up similarly to the initial screen using 1 µL of 2 µmol suspensions of each compound. Plates were incubated in SUNRISE™ Tecan microplate reader for kinetic measurement of growth every 15 mins for 24 h. Growth curves were analyzed in DB interface software and the effect of each compound on growth was evaluated based on the ratio of area under growth curve (compound/control) (Wallace I M, et al., Compound prioritization methods increase rates of chemical probe discovery in model organisms. *Chem. Biol.* 2011, 18(10): 1273-1283) as "no significant effect (ratio>0.5)", "inhibition (ratio≤0.5)", "static (ratio=0, bacterial growth revived after streak on a fresh NBY plate)" and "cidal (ratio=0, bacterial growth not revived)".

The purpose of this analysis was to identify compounds that were active against the pathogens and may possess novel mechanisms of action that convey selectivity for a specific pathogen. To study the active agents in greater detail, 77 compounds were selected for additional screening. It was attempted to ensure that these compounds had acceptable physicochemical properties for further development as potential therapeutic agents by prioritizing those based on i) their adherence to Lipinski's rule of 5, ii) meeting the criteria of the Golden triangle analysis, and iii) do not possessing obvious reactive functional groups. Additional selection criteria include the ability to rapidly functionalize the molecule through synthetic methods and the novelty of the structure. Based on these criteria, the unique compounds with bactericidal activity have been the primary focus of this effort. For this reason, several of these compounds were included with the compounds selected for additional screening.

Example 3

Germination and Phytotoxicity Assessment of Selected Compounds

The effect of selected compounds on seed germination and phytotoxicity was evaluated on both tomato and *Arabidopsis*. *Arabidopsis* seeds (cv. Columbia) were surface-sterilized by washing with 70% ethanol-0.05% Triton for 25 mins, followed by 100% ethanol for 10 mins. Molten 1% water agar was amended with each selected compound at a ratio of 1:100 (1 µL of 2 µmol compound:100 µL water agar) and added to wells of a 96-well plate. *Arabidopsis* seeds were suspended in sterilized water and 5 µL (approximately 10 seeds) was pipetted into each well in a 96-well plate. The germination rate of seed in each well was recorded 5 days later. Similarly, tomato seeds (cv. Tiny Tim) were treated with hot water to eliminate internal and external bacterial phytopathogens (Miller and Ivey, 2005). Five seeds were tested in each well in a 48 well-plate containing 100 µM amended 1% molten agar. The seed germination rate in each well was recorded 5 days later.

To determine whether a selected compound was phytotoxic, 1 µL of 2 µmol compound diluted in 100 µL water was applied to 10-day-old tomato seedlings in 96-well library tubes and 10-day-old *Arabidopsis* seedlings in 96-well plates. Death or abnormal growth of seedlings was assessed daily for 5 days. Controls of DMSO (1%), thymol (1.2%), and 2, 4-D (2%) were included in both seed and seedling tests.

Figure 2:
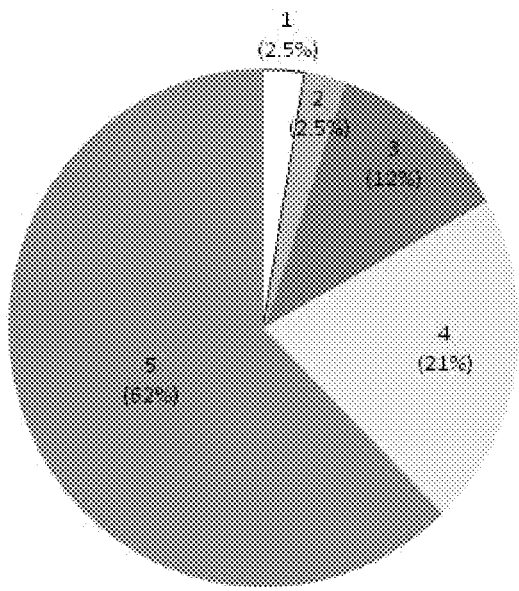
FIG. 2 is a pie chart showing the effect of selected compounds on multiple Cmm strains. Score 5=cidal to 5 groups of Cmm strains, 4=cidal to 4 groups of Cmm strain, 3=cidal to 3 groups of Cmm strain, 2=cidal to 2 groups of Cmm strain, 1=cidal to 1 group of Cmm strain.
Figure 10:
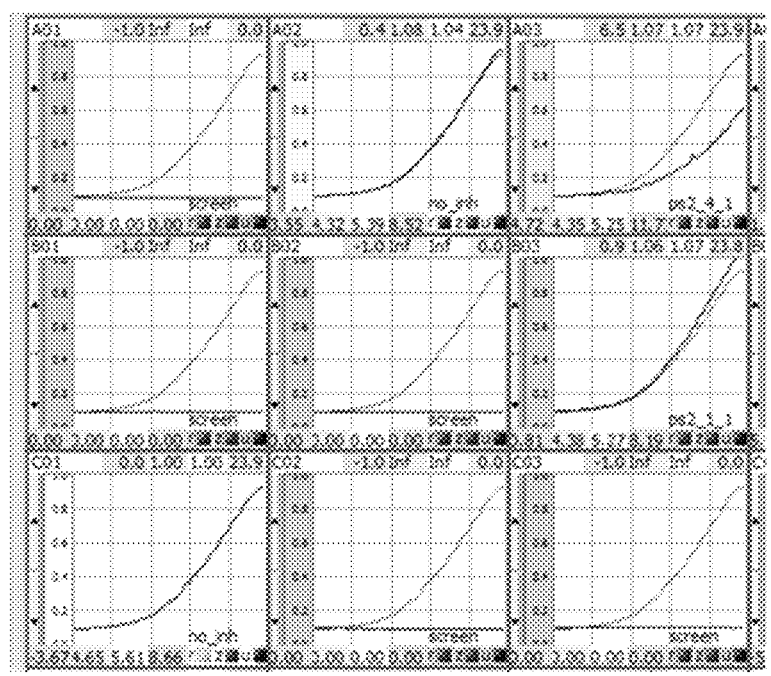
FIG. 10 displays the Yeast Grower (YG) software DB interface analysis of growth curve of 96-well plate (figure showed part of the plate). Well A01 was the blank control with NBY broth, B01 was the control with chloramphenicol, and C01 was the control without compound and A02, B02, C02, A03, B03, C03 were test wells with small molecules. The growth curve of C01 was setup as a reference curve (black in C01 and red in other wells) to compare the difference of growth.

In the secondary screen compounds were evaluated by kinetic measurement of Cmm growth over 24 h instead of end-point measurement used in the primary screen (FIG. 10). All the selected 77 compounds showed either a cidal or static effect on the five groups of Cmm strains tested, which confirmed the reproducibility of the results from the primary screen. Forty-eight of the candidates (62%) were cidal to all Cmm strains and 33% were cidal to at least three groups of Cmm strains (FIG. 2).

Figure 3A:
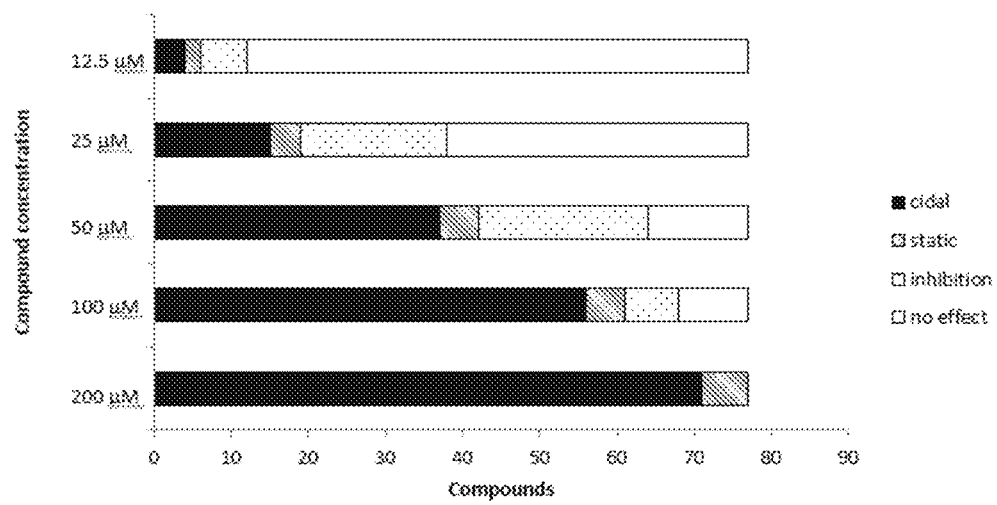
FIG. 3A is a chart showing the effect of serial diluted compounds on Cmm growth.
Figure 3B:
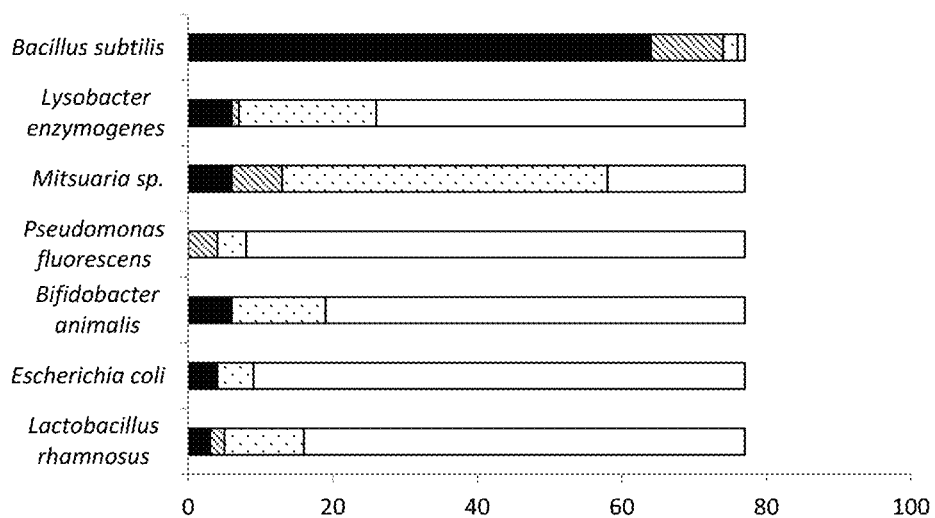
FIG. 3B is a chart showing the effect of select compounds on plant beneficial bacteria and human gut bacteria growth (the same legend in FIG. 3A applies in FIG. 3B).

While testing the compounds for minimum inhibitory concentration against Cmm, it was found that cidality was concentration dependent; half of compounds were no longer effective at 25 µM; at 12.5 µM four candidates were still cidal (FIG. 3A). To assess the specificity of the compounds, they were screened at 100 µM concentration against *P. fluorescens*, *L. enzymogenes*, (plant commensal bacteria) *B. animalis*, *E. coli*, and *Lactobacillus rhamnosus* (human gut commensal bacterium). Most compounds did not significantly affect the growth of plant and human beneficial bacteria (FIG. 3B). In contrast, the growth of the plant rhizospheric bacterium *B. subtilis* was completely inhibited by most compounds and the growth of *Mitsuaria* sp. was affected by more than half of the candidates.

Example 4

Effect of Compounds on Cmm Infection of Tomato Seedlings

A bioluminescent Cmm strain, BL-Cmm17, study (Xu X, et al., Bioluminescence imaging of *Clavibacter michiganensis* subsp. *michiganensis* infection of tomato seeds and plants. *Appl. Environ. Microbiol.* 2010, 76(12):3978-88) was used to monitor the effect of selected small molecules on Cmm infection of tomato seedlings in vivo Briefly, tomato seeds (cv. OH9242) were infested by soaking in BL-Cmm17 suspension ($10^8$ CFU/mL) in a 100-ml sterilize beaker. The beaker was placed in a Nucerite Desiccator (Nalge Sybron Corporation, Rochester, N.Y.), and a vacuum was applied for 5 min using an Air Cadet pump (Barnant, Barrington, Ill.) with a maximum of 18 lb/in$^2$ pressure. Seeds treated similarly with sterilized water were used as controls. After inoculation, seeds were air-dried and one seed was placed in a 1.2 mL library tube containing 400 µL of 1% water agar; tubes were placed in wells of a 96-well plate. The selected compound (1 µL of 2 µmol in 50 µL water) was applied to each seed and the plate was incubated at 25° C. under 8 h/16 h light/dark conditions. There were three replicate seeds/plate per treatment. Bioluminescence images were taken using an in vivo imaging system (IVIS Model 100; Xenogen, CA) 3 and 8 days later. Eight-day-old seedlings were ground in potassium phosphate buffer and extracts were serially diluted and plated on NBY to assess the presence of Cmm.

Some compounds reduced the germination of *Arabidopsis* seeds. All non-treated *Arabidopsis* seeds germinated, whereas the rate of germination for seeds treated with DMSO alone was 85%. Forty-one of 77 (53%) compounds had no or little effect on *Arabidopsis* germination (≥80%), 15 candidates moderately reduced germination (50%~80%), and 21 candidates reduced germination rates to less than 50% (Table 2).

TABLE 2

The compounds effect on *Arabidopsis* and tomato seed germination.

| Germination rate (%) | score | Number of compounds | |
|---|---|---|---|
| | | *Arabidopsis* | tomato |
| 100 | 4 | 24 | 71 |
| 80 ≤ GR < 100 | 3 | 17 | 1 |
| 50 ≤ GR < 80 | 2 | 6 | 2 |
| <50 | 1 | 30 | 3 |

The majority of hit compounds (93%) did not affect tomato seed germination compared to untreated and DMSO controls. The germination rate of tomato control seeds, both non-treated and DMSO treated was 100%. Only six compounds reduced germination. Compounds applied to seedlings did not cause deformation or death in either *Arabidopsis* or tomato. Together the data on both *Arabidopsis* and tomato seeds suggest that the majority of the compounds are specific to bacteria at the doses tested.

Figure 4:
FIG. 4 is a group of bioluminescence images of tomato seed infested with BL-Cmm17 and treated with selected small molecules in 96-well library tube. Images were taken on 8-day old seedlings with in vivo imaging system (IVIS, Xenogen). Rows 1 and 2 (all columns) were infected seeds and treated with small molecules; Row 3, column 1 were infected seeds and treated with small molecules; Row 3, column 2 (F through H) were infected and treated with DMSO; Row 3, column 3 (A through H) were infected seeds and not treated with small molecules; and Row 3, column 4 (A through H) were non-inoculated healthy seeds.
Figure 5:
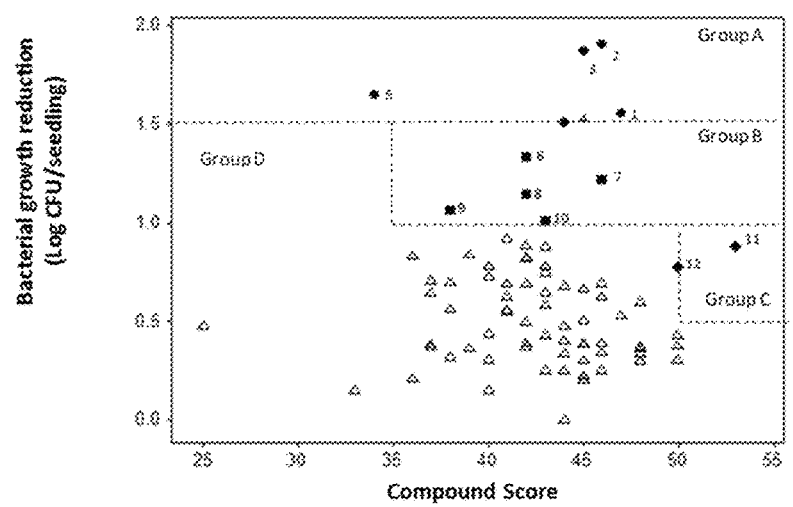
FIG. 5 is a plot showing compound selection based on its effect on reduction of bacterial growth in infected tomato seedlings and compound score. Compounds were categorized into four groups: Group A included compounds (1-5) with bacterial growth reduction over 1.5 log; Group B included compounds (6-10) with bacterial growth reduction over 1.0 log and score over 35; Group C included compounds (11 and 12) with bacterial growth reduction over 0.5 log and score over 50; and Group D included compounds that did not reach the criteria for Group A, B or C.

The bioluminescent Cmm strain BL-Cmm17 is a virulent strain carrying luxCDABE and is a useful reporter because the strength of luminescent signals is positively correlated with the number of live cells (Xu et al., 2010). Bioluminescent imaging of inoculated tomato seedlings showed that the non-treated, infected tomato seedlings exhibited high luminescent signals compared to Cmm-inoculated seedlings treated with most compounds. Seedlings treated with nine of 77 compounds exhibited high luminescent signals, indicating that these compounds did not inhibit Cmm infection (FIG. 4). However, half of the compounds reduced the tomato Cmm burden by over 0.5 log CFU; 10 compounds reduced Cmm populations by 1 log or greater (FIG. 5).

Figure 6:
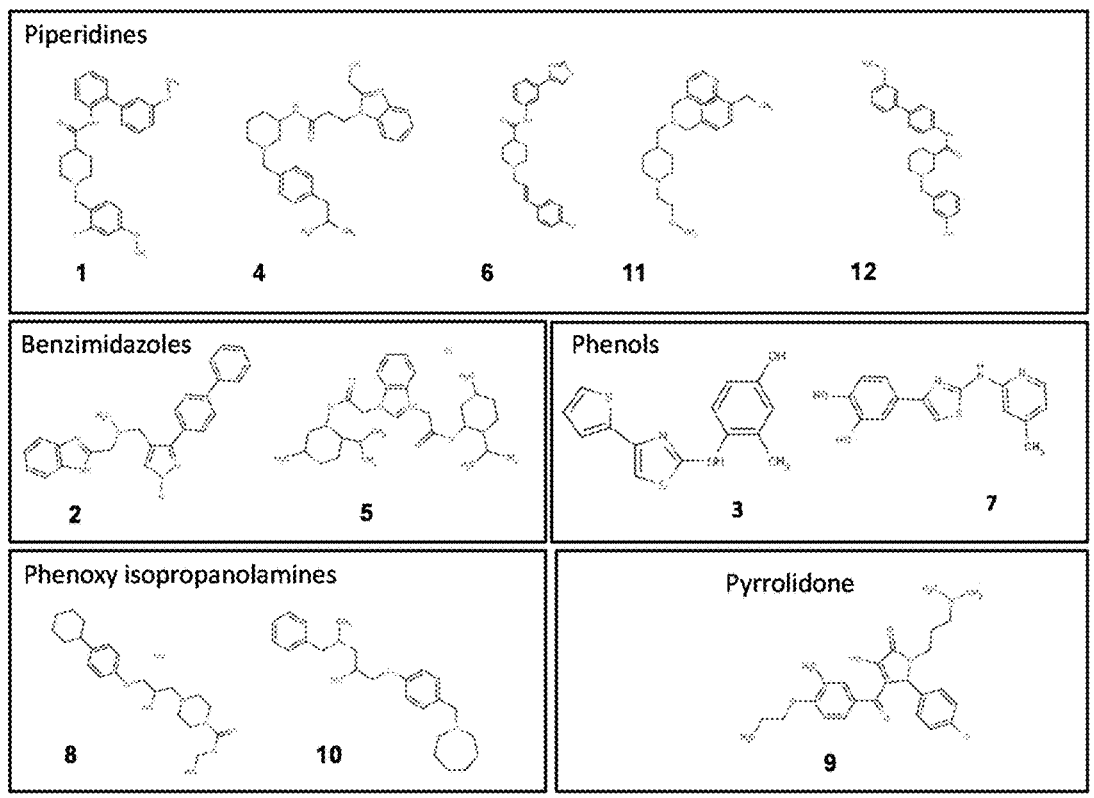
FIG. 6 displays the chemical structures of the 12 most potent small molecules (e.g., compounds 1-12).

The minimum and maximum sum scores for specificity, sensitivity and phytotoxicity in the secondary screen were 14 and 57, whereas the actual score ranged from 25 to 53. A scatter plot of the compound scores versus effect on Cmm seedling infection allowed us to categorize these compounds into four groups (FIG. 5). The most potent compounds were identified by considering both the effect on reduction of Cmm infection in seedlings and high score in the secondary screen. Thus, compounds 1 to 12 from Group A, B and C were considered to have a strong potential for bactericide development. The chemical structures of the 12 compounds falls into five distinct classes: piperidines, benzimidazole, phenols, phenoxy isopropanolamines and pyrrolidones (FIG. 6).

Example 5

Cytotoxicity of Selected Compounds

Caco-2 cells (human colonic carcinoma) were obtained from the American Type Culture Collection, Rockville, Md., and maintained in growth medium [Minimal Essential Medium (MEM) supplemented with 20% Fetal Bovine Serum (FBS), 1% non-essential amino acid (NEAA, Invitrogen Life Technologies, NY) and with 1 mM sodium pyruvate] at 37° C. in a humidified, 5% $CO_2$ incubator. LDH Cytotoxicity assay was performed following the manufacturer's instructions (LDH Cytotoxicity Assay Kit, PIERCE™, Thermo Scientific, IL). Briefly, approx. $1.4 \times 10^5$ cells were grown in a 96-well tissue culture plate with 150 µL of growth medium and incubated for 24 h at 37° C. in a humidified, 5% $CO_2$ incubator until a monolayer was completely formed. After three washes with medium without supplements, 1 µL of 2 µmol compound was added to each well and incubated for 4 h at 37° C. in a humidified, 5% $CO_2$ incubator. 50 µL of cell supernatant were collected and LDH was measured using the controls indicated by the kit. Blank controls were used by adding 1 µl of DMSO and values subtracted from the readings.

Figure 7:
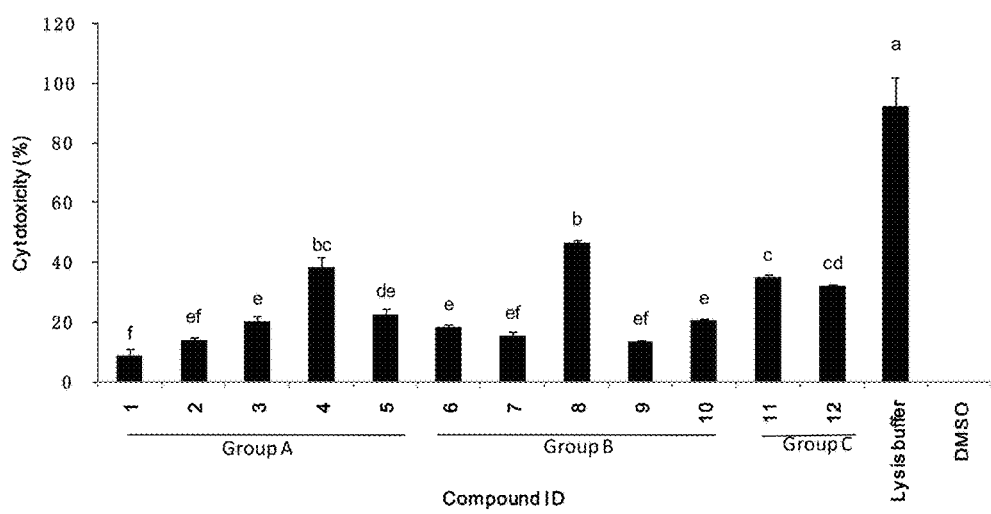
FIG. 7 is a plot showing cytotoxicity evaluation of the compounds 1-12. Cytotoxicity was assessed using Caco-2 cells exposed to 100 µM of compound for 4 hours.

Cytotoxicity was evaluated using cultured mammalian cells to explore the potential future application of these top selected compounds on tomato for consumption. The 12 compounds tested showed a range of cytotoxicity of 8.4% to 46.6% in the cytotoxicity assay (FIG. 7), compared to the lysis buffer control. These results suggested that the most potent compounds show varying degrees of specificity to bacteria with minor degrees of general toxicity.

Discussion

Here the results of an HTP-growth screen to identify novel anti-Cmm compounds are reported. Twelve such drug-like small molecule compounds were identified that satisfied the pre-defined criteria. The initial goal of the project was to (i) exploit the pre-selected library to identify hits that completely inhibit the growth of Cmm; (ii) further discover such small molecules that vary in growth inhibition of Cmm and other bacteria using a kinetic study as previously described (Wallace et al., 2011); and (iii) test these small molecules on pathogen infection in the host. By using a library of pre-screened, bioactive compounds, it has been found that the hit rate in such screens against untested organisms is increased between 4 and 12-fold (Wallace et al., 2011; Lieberman L A, et al., A small-molecule screen identifies the antipsychotic drug pimozide as an inhibitor of *Listeria monocytogenes* infection. *Antimicrob. Agents Chemother.* 2009, 53 756 64). Specifically the yeast active "yactive" library was chosen, and screened 4,200 of the 7,500 compounds (selected from a total of 81,000 compounds) that have previously shown inhibitory to *Saccharomyces cerevisiae* growth by at least 30%. Consistent with the reported increase in hit-rate with this library, the hit rate in this study was high (11.1%), despite the strict threshold criteria used to select candidates based on Cmm growth inhibition.

Depending on the screening purpose, different cellular and molecular HTS approaches have been developed, and each have different criteria for hit selection. For example, according to a study performed at 12.5 µM, hit rates of 0.024% for *E. coli* and 0.005% for *P. aeruginosa* were observed (De La Fuente, R et al., Small molecules with antimicrobial activity against *E. coli* and *P. aeruginosa* identified by high-throughput screening. *Br J Pharmacol.* 2006, 149(5):551-9). This study for complete Cmm inhibition (also performed at 12.5 µM), in contrast, showed numbers comparable to classical antibiotics and were 46-fold higher than those reported for *E. coli*.

Compared to the end-point value used in the primary screen, the area under the growth curve calculated by kinetic measurement of growth provides more quantitative data to evaluate compound effect on growth inhibition (Wallace et al., 2011). Therefore, in the secondary screen, the selected 77 compounds were tested on additional Cmm strains as well as other bacteria using kinetic OD reader. As expected, the majority of compounds showed cidal effect on growth of multiple Cmm strains, but some compounds were static rather than cidal to diverse strains. Since the Cmm strains were collected from different geographic locations and also presented different DNA fingerprint profiles, their compound sensitivity is likely due to their genetic diversity. Interestingly, testing the compounds on other plant beneficial bacteria and human gut bacteria showed that most compounds were cidal against the Gram-positive bacterium *B. subtilis*, but had little or no effect on the Gram-negative bacteria tested. These observations suggest that the compounds tested in the second screen may disrupt the cell membrane structure or metabolic activity specific in Gram-positive bacteria.

The cell-based HTP screens rely on bacterial growth inhibition, hence they will miss virulence genes that when inhibited do not show a growth defect. However, the rapid, high-throughput, in vivo imaging assessment of Cmm infection in tomato may provide a complementary way to identifying small molecules that influence virulence genes or induce plant defenses.

The top 12 drug-like compounds populate five distinct classes (FIG. 6). The benzimidazole-containing compound carbendazim is a well-known fungicide widely used in agricultural production (Zikos C, et al., Commercially available chemicals as immunizing haptens for the development of a polyclonal antibody recognizing carbendazim and other benzimidazole-type fungicides. *Chemosphere.* 2015, 119 Suppl:S16-20). In addition, recently benzimidazole class of compounds have been shown to inhibit a G+ bacterium, *Staphylococcus aureus* by targeting DNA gyraseB enzyme. Two benzimidazole compounds (2 and 5) with specific anti-Cmm activity were found. In particular, compound #5 with a lower score in the secondary screen exhibited a broader antibacterial spectrum compared with other 11 compounds in this study. A few phenolic compounds have been studied for their antimicrobial activity and two natural phenols were less effective against Gram-negative bacteria compared to Gram-positive bacteria (King A D Jr, et al., Antimicrobial properties of natural phenols and related compounds: obtusastyrene and dihydro-obtusastyrene. *Antimicrob. Agents Chemother.* 1972, 1(3):263-7). In addition, a phenol drug was found to inhibit *B. subtilis* growth by interfering with cell wall synthesis (Shimi I R, et al., 4,4'-isopropylidine-bis(2-isopropyl)phenol, a new inhibitor for cell wall formation of *Bacillus subtilis. Antimicrob. Agents Chemother.* 1976, 9(4):580-4). Consistent with this, two phenol compounds, #3 and #7, were identified that were cidal to both Cmm and *B. subtilis*, but not to the Gram-negative bacteria tested. Hence it was suspected that these phenols have a similar mode of action. Almost half of the 12 top potent compounds belong to piperidines, however, there are very few reports on this class of compounds. A recent study claimed piperidines to possess antimicrobial effects (Patel et al., 2012). Only one of the top compounds, #9, fell into pyrrolidone class, but several previous studies have discussed pyrrolidone derivatives against human bacterial pathogens (Sathiyanarayanan G., et al., Optimization and production of pyrrolidone antimicrobial agent from marine sponge-associated *Streptomyces* sp. MAPS15. *Bioprocess Biosyst. Eng.* 2014, 37(3):561-73; Phaechamud T, et al., Characterization and Antimicrobial Activity of N-Methyl-2-pyrrolidone-loaded Ethylene Oxide-Propylene Oxide Block Copolymer Thermosensitive Gel. *Indian J. Pharm. Sci.* 2012, 74(6):498-504). Compounds #8 and #10 were the first phenoxy isopropanolamines reported to have antibacterial activity.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A seed coated or primed with a compound having Formula I:

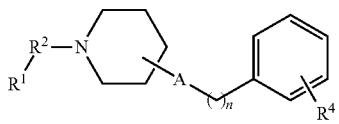

I wherein

A is —C(O)—NR$^3$— or —NR$^3$—C(O)—;

n is 0, 1, or 2;

R$^1$ is an aryl or heteroaryl, optionally substituted with one or more hydroxyl, halogen, alkyl, alkenyl, alkynyl, alkoxyl, alkenyloxyl, amino, aminoalkyl, aminoalkenyl, cycloalkyl, cycloalkenyl, alkylcarboxylate, cycloalkylcarboxylate, alkylcarbonate, cycloalkylcarbonate, amidoalkyl, amidocycloalkyl, aryl or heteroaryl;

R$^2$ is a C$_{1-4}$ alkylene, C$_{1-4}$ alkoxylene, or C$_{3-5}$ alkenylene, optionally substituted with hydroxyl, halogen, oxo, amino, or C$_{1-6}$ alkyl;

R$^3$ is H or C$_{1-6}$ alkyl; and

R$^4$ is an aryl or heteroaryl, optionally substituted with one or more hydroxyl, halogen, alkyl, alkenyl, alkynyl, alkoxyl, alkenyloxyl, amino, aminoalkyl, aminoalkenyl, cycloalkyl, cycloalkenyl, alkylcarboxylate, cycloalkylcarboxylate, alkylcarbonate, cycloalkylcarbonate, amidoalkyl, amidocycloalkyl, aryl or heteroaryl;

or an agriculturally suitable salt thereof.

2. The seed of claim 1, wherein the compound is chosen from:

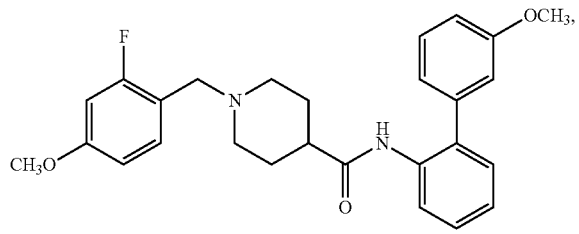

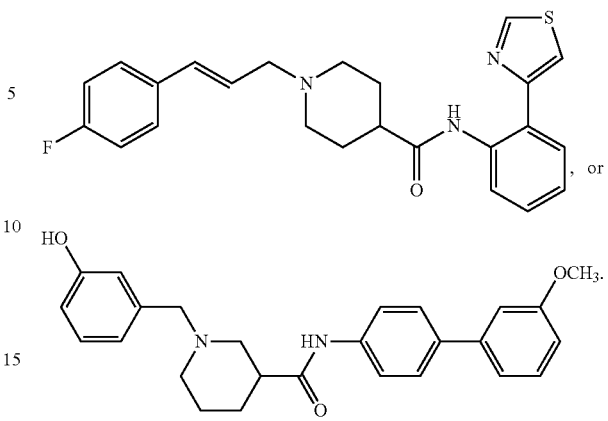

3. A formulation, comprising: the seed of claim 1 and a soil-compatible carrier.

4. The formulation of claim 3, wherein the soil-compatible carrier is chosen from bran, starch, cellulose, alginate, clay, pectin, carboxy methyl cellulose and mixtures thereof.

5. The seed of claim 1, wherein the seed is a tomato seed.

6. The seed of claim 1, wherein the seed is a corn seed, bean seed, potato seed, wheat seed, or alfalfa seed.

7. A compound, wherein the compound is chosen from:

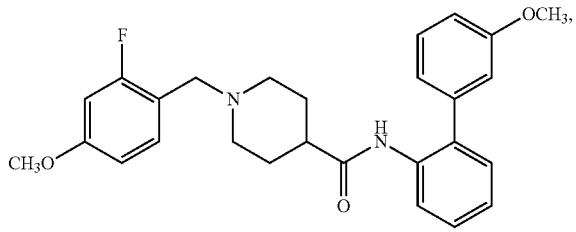

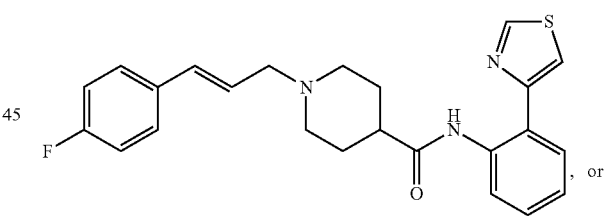

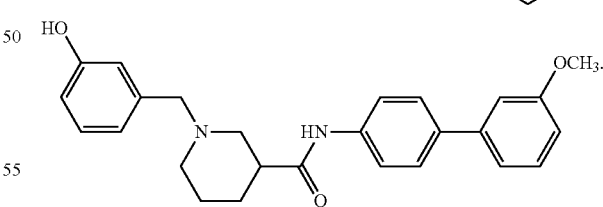

* * * * *